United States Patent
Seth et al.

(10) Patent No.: US 7,684,654 B2
(45) Date of Patent: Mar. 23, 2010

(54) SYSTEM AND METHOD FOR FAULT DETECTION AND RECOVERY IN A MEDICAL IMAGING SYSTEM

(75) Inventors: Anuj Seth, Karnataka (IN); Jigney N. Shah, Waukesha, WI (US); Vinay Parthan, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 997 days.

(21) Appl. No.: 10/881,675

(22) Filed: Jun. 30, 2004

(65) Prior Publication Data

US 2006/0005081 A1  Jan. 5, 2006

(51) Int. Cl.
G06K 9/03 (2006.01)
(52) U.S. Cl. ...................... 382/309; 714/704
(58) Field of Classification Search ................ 302/709; 714/2, 4, 5, 748, 55, 704, 706; 702/182, 702/185; 382/309
See application file for complete search history.

(56) References Cited

U.S. PATENT DOCUMENTS

| 5,295,258 | A | * | 3/1994 | Jewett et al. ................. 714/12 |
| 5,440,726 | A |   | 8/1995 | Fuchs et al. |
| 5,903,717 | A | * | 5/1999 | Wardrop ...................... 714/12 |
| 5,948,112 | A |   | 9/1999 | Shimada et al. |
| 6,141,785 | A | * | 10/2000 | Hur et al. ..................... 714/748 |
| 6,308,328 | B1 | * | 10/2001 | Bowcutt et al. ............. 725/111 |
| 6,567,937 | B1 |   | 5/2003 | Flores et al. |
| 6,654,801 | B2 | * | 11/2003 | Mann et al. ................. 709/224 |
| 6,725,392 | B1 | * | 4/2004 | Frey et al. ...................... 714/6 |
| 6,883,000 | B1 | * | 4/2005 | Gropper ...................... 707/10 |
| 7,032,132 | B2 | * | 4/2006 | Adachi ........................ 714/28 |
| 7,143,305 | B2 | * | 11/2006 | Hajji et al. ..................... 714/2 |
| 2003/0135389 | A1 |   | 7/2003 | Gudapakkam et al. |
| 2003/0214953 | A1 | * | 11/2003 | El-Demerdash et al. ..... 370/400 |
| 2003/0217309 | A1 |   | 11/2003 | Lodrige |
| 2004/0010716 | A1 | * | 1/2004 | Childress et al. ............ 713/201 |

* cited by examiner

*Primary Examiner*—Bhavesh M Mehta
*Assistant Examiner*—Dennis Rosario
(74) *Attorney, Agent, or Firm*—Armstrong Teasdale LLP

(57) ABSTRACT

A system and method for fault detection and recovery in a medical imaging system are provided. The method includes monitoring operations of a plurality of subsystems of the medical imaging system and determining if an error has occurred in a subsystem based on the monitoring. The method further includes identifying at least one component within the subsystem having the determined error and automatically restoring the at least one component in the identified subsystem having the determined error.

30 Claims, 7 Drawing Sheets

| Stable State | Actor | Severity Level |
|---|---|---|
| Idle | Actor 202 | 4 |
| Apparatus Setup | Actor 202 | 3 |
| Exam Started | Actor 202 | 2 |

| Stable State | Actor | Severity Level |
|---|---|---|
| Idle | Actor 204 | 1 |
| Apparatus Setup | Actor 204 | 1 |
| Exam Started | Actor 204 | 1 |

FIG. 4

```
# Example configuration file
<begin>
[FAULT_RECOVERY]
PingInterval.Type  = Number
PingInterval.Val  = 5

ActorNames.Type = StringList
ActorNames.Val = { Actor202, Actor204 }
ActorExecutables.Type = StringList
ActorExecutables.Val ={ Actor202.lnx, Actor204.lnx}
StableStates.Type = StringList
StableStates.Val  { IDLE, APPSETUP, EXAM_STARTED}

[FAULTS_CONFIG]
FaultsCount.Type = Number
If Actor202 crashes in IDLE state, it is a
severity 3 fault
FaultsCount.Val= 2
Fault0.Type = StringList
If Actor202 crashes in EXAM_STARTED state,
it is a severity 1 fault
Fault0.Val = {IDLE, Actor202, SEV_3}
Fault1.Type = StringList
Fault1.Val  = {EXAM_STARTED, Actor204, SEV_1}

<end>
```

FIG. 5

SYSTEM AND METHOD FOR FAULT DETECTION AND RECOVERY IN A MEDICAL IMAGING SYSTEM

BACKGROUND OF THE INVENTION

The invention relates generally to medical imaging systems, and more particularly, to a system and method for fault detection and recovery in such medical imaging systems.

Medical imaging systems, such as, for example, computer tomography (CT) systems, X-ray systems, magnetic resonance imaging (MRI) systems, positron emission tomography (PET) systems and the like, are defined by a number of subsystems that interact to deliver the functionalities for these systems. In an X-ray scanner, such subsystems include, but are not limited to an X-ray generator, a table positioner, a system control and an operator console. These subsystems are typically different physical computer systems running on different operating systems.

The subsystems may be further subdivided into software applications or other logical subsystems. These software applications are typically object oriented programs that individually or in combination with other software applications perform specific functionality. For example, the functionality may include image acquisition, image processing, etc.

The complexity in software applications and the interrelationship between applications has increased. This also has increased the criticality of faults and their occurrence. In medical imaging systems, testing and maintenance reduces the likelihood of these faults, however, faults and errors still occur. This then may result in X-Ray scanner downtime, thereby decreasing throughput (e.g., reducing the medical procedures that can be performed) and increasing costs.

Additionally, known techniques in fault management in medical imaging systems require rebooting the whole medical imaging system, even for a fault that is not hardware based or that only affects specific components within the system. This reduces the operating time of the medical imaging system, which again reduces throughput and increases costs.

BRIEF DESCRIPTION OF THE INVENTION

In one exemplary embodiment, a method for controlling a medical imaging system is provided. The method includes monitoring operations of a plurality of subsystems of the medical imaging system and determining if an error has occurred in a subsystem based on the monitoring. The method further includes identifying at least one component within the subsystem having the determined error and automatically restoring the at least one component in the identified subsystem having the determined error.

In another exemplary embodiment, a medical imaging system having a plurality of subsystems is provided. The subsystems each further include at least one component. The medical imaging system further includes a subsystem controller for each of the plurality of subsystems and communicating with the at least one component in each of the subsystems. The subsystem controller is configured to identify components within the subsystem failing to respond to a request for a response and to reset the component failing to respond. The medical imaging system additionally includes a system manager communicating with each of the plurality of subsystem controllers and is configured to communicate a failure to respond to each of the subsystem controllers.

BRIEF DESCRIPTION OF THE DRAWINGS

FIG. 4 illustrates charts showing exemplary severity levels in accordance with an exemplary embodiment of the invention.

FIG. 5 is an exemplary configuration file in accordance with an exemplary embodiment for use in various embodiments of the invention to assign severity level values to actors.

DETAILED DESCRIPTION OF THE INVENTION

Various embodiments of the invention provide fault management and recovery in a medical imaging system, including, for example, recovery due to software related faults. Software related faults may include, but are not limited to, a crash, hang up, lock-up, failure, error and/or other undesirable process that may lead to the malfunctioning of the software or medical imaging system. Further, the medical imaging system of the various embodiments, may include, for example, a Computer Tomography (CT) Scanner, Medical Resonance Imaging (MRI) Scanner, Positron Emission Tomography (PET) Scanner, Ultrasound Scanner, and/or an X-ray Machine.

In general, the various embodiments provide fault management and recovery performed based on different levels of severity of the fault. The different levels of severity of the various embodiments of the invention determine in part the interaction and operation of the hardware in the fault recovery process. As a result, the reboot of the medical imaging system is only required in some cases, for example, if the fault related to both software and hardware of the medical imaging system. In operation, the fault recovery mechanism of the various embodiments of the invention returns the component or the medical imaging system to the stable state, for example, in which it was operating before the fault. In general, the stable states of a medical imaging system include, but are not limited to, system idle, application setup, and exam-started state. The system idle state represents a state wherein no operations are being performed on a medical imaging system. The application setup state represents the condition wherein the radiologist/user selects the application protocols to perform on the patient. Further, the exam-started state represents a state wherein a medical exam is being performed on a medical imaging system.

Figure 1:
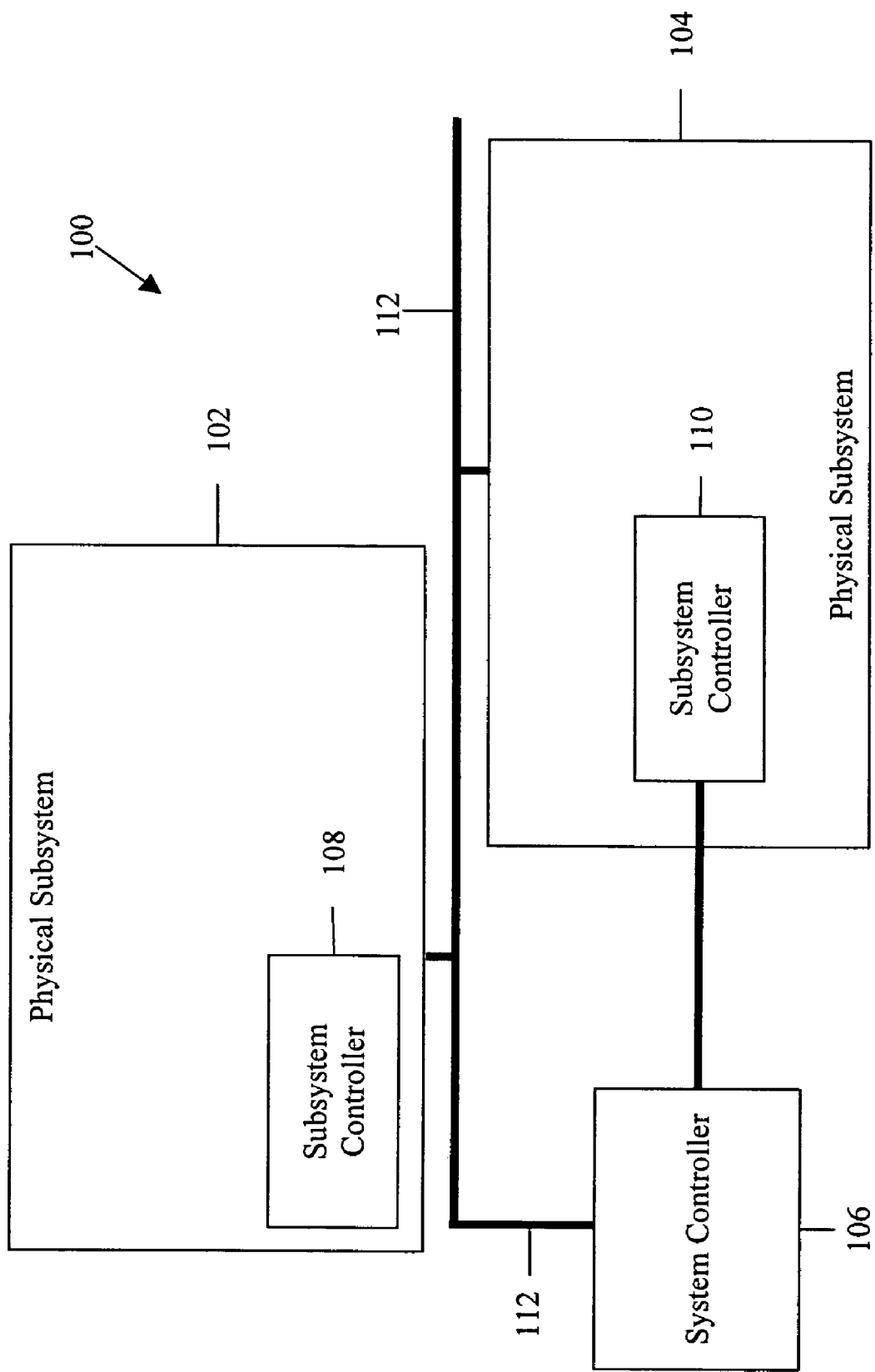
FIG. 1 is block diagram of a medical imaging system constructed in accordance with an exemplary embodiment of the invention.

FIG. 1 shows a medical imaging system 100 that performs fault management and recovery in accordance with various embodiments of the invention. Medical imaging system 100 in its various embodiments includes one or more physical subsystem, for example, a physical subsystem 102 and a physical subsystem 104. Further, medical imaging system 100 also includes one or more system managers 106, a subsystem controller 108 and 110 associated with each physical subsystem 102 and 104, and a communication link 112. The physical subsystems 102 and 104 include, for example, physical processing or operating components or entities that perform different operations in medical imaging system 100, and in various embodiments are implemented as, but not limited, physical computer systems running on different operating systems. For example, in an X-ray machine, the physical subsystems included are an X-ray generator, a table positioner, a system control and an operator console.

In various embodiments, a plurality of subsystem controllers, for example, subsystem controller 108 and subsystem controller 110 may be provided in physical subsystem 102 and physical subsystem 104, respectively. System manager 106, subsystem controller 108, and subsystem controller 110 may be software components or algorithms that interact with each other for use in recovering medical imaging system 100 and/or physical subsystem 102, and physical subsystem 104 from faults or errors. Further, the functioning, components, and the properties of subsystem controller 108 and subsystem controller 110 may be the same or different as desired or needed. Subsystem controller 108 and subsystem controller 110 ensure that all software components in physical subsystem 102 and physical subsystem 104 respectively, continue to function correctly. System manager 106 ensures that all the subsystem controllers that are a part of its system continue to function correctly. This hierarchy ensures that all subsystems controllers monitor their subsystems while system manager 106 ensures that all the subsystem controllers continue to operate correctly.

In various embodiments of the invention, the communication link in medical imaging system 100 between physical subsystem 102, physical subsystem 104, and system manager 106 is provided via communication link 112. Communication link 112 enables platform (e.g., operating system) independent interoperability between a plurality of physical subsystems. In various embodiments, communication link 112 is, for example, enabled through a Shared Memory Communication, or a Common Object Request Broker Architecture (CORBA®) based architecture. In the CORBA based architecture, for example, subsystem controller 108 and system manager 106 expose interfaces through which the Interface Definition Language (IDL) using direct method calls can be made for communication.

Figure 2:
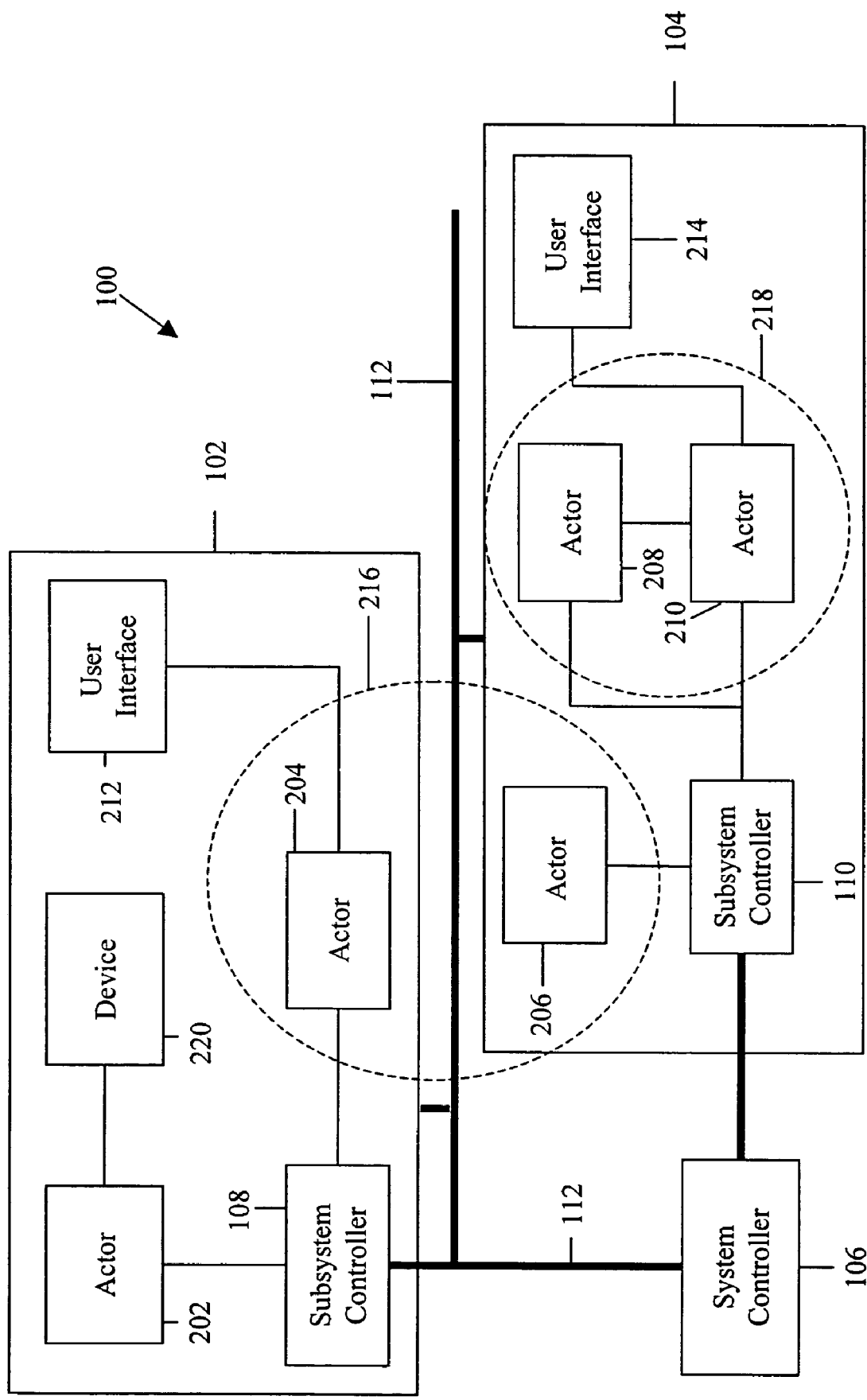
FIG. 2 is a detailed block diagram showing the sub-elements of the medical imaging system of FIG. 1.

FIG. 2 shows various components of physical subsystem 102 and physical subsystem 104, and the logical links between these components. In various embodiments of the invention, physical subsystem 102 includes an actor 202, and an actor 204, and physical subsystem 104 includes an actor 206, an actor 208, and an actor 210. In various embodiments, an actor may be, for example, a software component that may be algorithmic or may be a wrapper object for a physical hardware device. In addition, an actor also may store information such that it is able to return to an existing stable state as described in more detail herein. Such information, may include, for example, the current stable state of an actor and persistent data associated with this state. Persistent data may include, for example, data relevant for the actor to rollback or return to the state at which it was prior to the fault. Such data may include, for example, the application protocols selected, etc. Further, such information may be stored, for example, in a secondary storage medium such as hard disk, Storage Area Network (SAN), Redundant Array of Independent Disks (RAID) data storage.

It should be noted that, for example, in an Atlas system, a unique set of entities may be included to provide the fundamental functions of the system and provide means to perform these functions such as is described in U.S. Patent Application Publication No. US 2003/0135389 and entitled "Method and Apparatus for Managing A Distributed X-Ray System." These functional entities may be referred to as Atlas Actors or actors. Actors cooperate to achieve general system operation required by an application. For example, an image detector actor converts an X-ray pattern resulting from the interaction of the X-ray beam with the patient, into a usable information object referred to as an image. As another example, an Acquisition Synchronizer actor coordinates the actions of the different actors in the system.

It should be noted that, for example, actors in a system, such as in an Atlas system as described in co-pending U.S. patent application Ser. No. 2003/0135389 A1, entitled "Method and Apparatus for Managing a Distributed X-ray System," the entire disclosure of which is hereby incorporated by reference herein, may be provided by a unique set of entities that provide the fundamental functions of the system and provide means to perform these functions. These functional entities may be referred to as Atlas Actors or actors. Actors cooperate to achieve general system operation required by an application. For example, an image detector actor converts an X-ray pattern resulting from the interaction of the X-ray beam with the patient, into a usable information object referred to as an image. As another example, an Acquisition Synchronizer actor coordinates the actions of the different actors in the system.

Further, actor 204 and actor 206, and actor 208 and 210 operate to form a logical subsystem 216 and a logical subsystem 218, respectively. A logical subsystem may be configured as, for example, a functional module containing one or more actors that are interdependent in order to perform a specific action in medical imaging system 100. The functionality, for example, may be an operator console functionality of X-ray scanner. Examples of functional modules as are known include, Athena the Image Processing Subsystem, Saber the Positioner Subsystem, Calypso the System Control Subsystem. Additionally, it should be noted that the logical subsystems may be provided across physical subsystems.

In various embodiments of the invention, the functioning of actor 202 and actor 204 is monitored by subsystem controller 108, and the functioning of actor 206, actor 208, and actor 210 is monitored by subsystem controller 110. In addition, if a fault occurs in the respective actors, subsystem controller 108 and subsystem controller 110 also notify, for example, actors dependent on the actor having the fault and log an appropriate error.

Further, in various embodiments, physical subsystem 102 and physical subsystem 104 further include a user interface 212 and a user interface 214, respectively. User interface 212 and user interface 214 are configured to receive user inputs and communicate the inputs to actor 204 and actor 210, respectively, for processing. The actors also may be linked to devices, for example, actor 202 is linked to device 220. Examples of devices 220 include, but are not limited to, an exposure regulating device, an input device controlling the height of an exam table, a printer, a positioner, a detector, etc.

Figure 3:
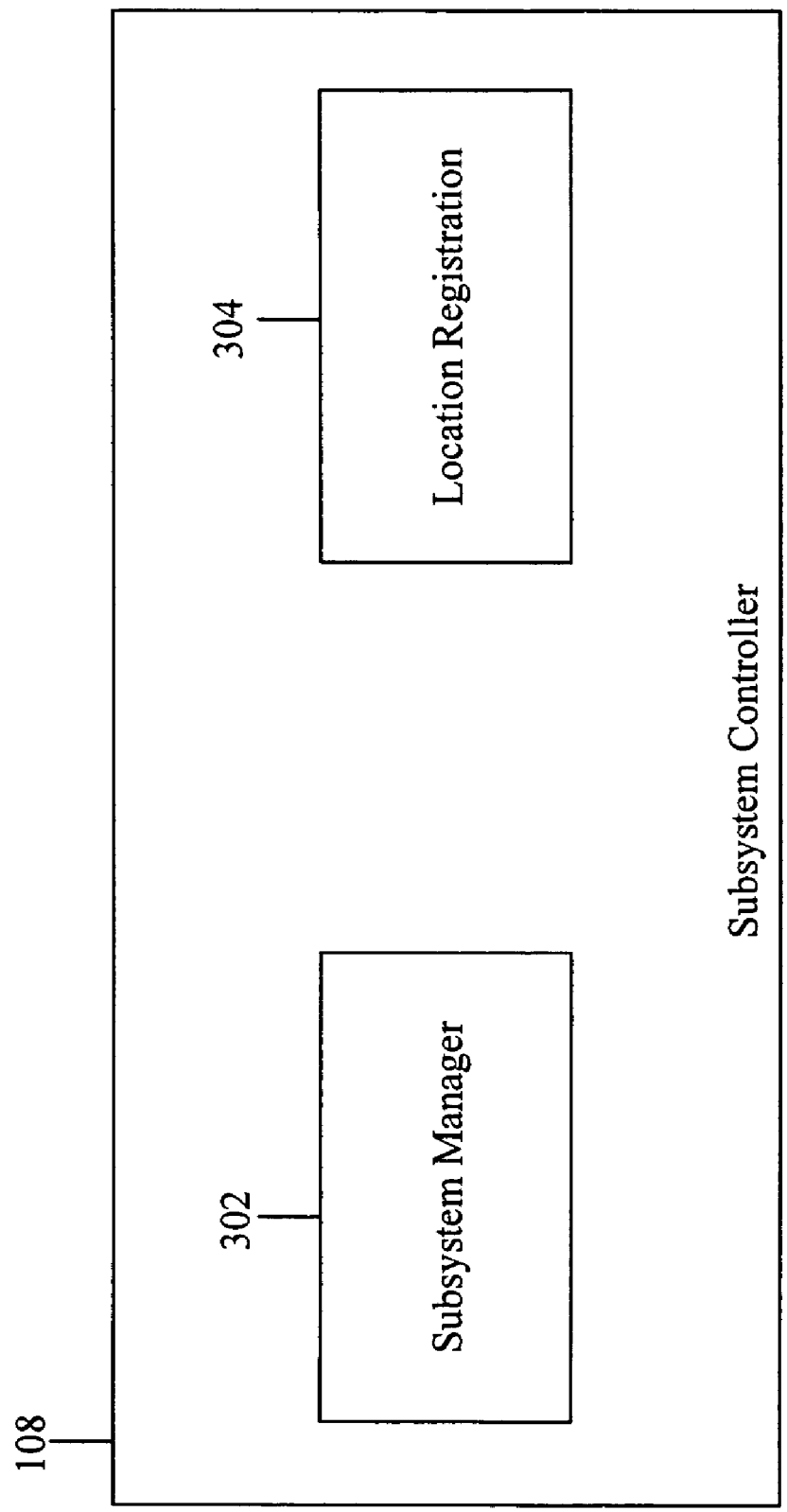
FIG. 3 is a block diagram of a subsystem controller in accordance with an exemplary embodiment of the invention that may be used in connection with the medical imaging system of FIG. 1.

FIG. 3 shows the subcomponents of subsystem controller 108. It should be noted that the same subcomponents may also be provided in subsystem controller 110. In various embodiments of the invention, subsystem controller 108 includes a subsystem manager 302 and a location registration component 304. Subsystem manager 302 monitors the functioning of the actors, for example, actor 202 and actor 204. The functioning is monitored by a system control mechanism, wherein subsystem manager 302 pings (e.g., sends a request for a response) the respective actors and waits for their response. If a response is not received, subsystem manager 302 may communicate with system controller 106 and generate an appropriate fault recovery mechanism as described in more detail herein with reference to FIG. 4. In various embodiments of the invention, subsystem manager 302 also logs any errors and provides appropriate commands or control actions (e.g., to stop operation corresponding to an actor). The commands or control actions may be generated, for example, based on the severity of the error. For example, if a less critical fault occurs in actor 202, subsystem manager 302 may only restart actor 202. However, if a more severe fault occurs, subsystem manager 302 may communicate a reboot command to system manager 106, and system manager 106, in response, reboots medical imaging system 100. Subsystem manager 302 also may restore or reset the component that has a fault to a stable state (e.g., system idle application setup, and/or exam-started stable state).

In one exemplary embodiment of the invention, one location registration component may be provided for each physical subsystem (e.g., one location registration component 304 present in physical subsystem 102). Location registration component 304 registers actor 202 and actor 204 with their functionalities and their dependencies and interdependencies on other actors in medical imaging system 100. Location registration component 304 also communicates with other location registration components in physical subsystem 104 to generate logical connections. For example, location registration component 304 may communicate with corresponding location registration component 304 (not shown) in physical subsystem 104 to form a logical connection between actor 204 and actor 206. In an alternate embodiment of the invention, there may be a single location registration component 304 provided for the entire medical imaging system 100, which may register all the actors with their dependencies and interdependencies.

In various embodiments of the invention, fault recovery is based on different levels of fault identified by the subsystem controllers, including, for example, subsystem controller 108 and subsystem controller 110. The faults relating to each actor in different states are identified and stored in a pre-defined configuration file, which is used by a subsystem controller to determine how to recover from the fault. FIG. 4 shows an exemplary illustration of the possible states for actor 202 and actor 204. In an idle state, for example, a fault in actor 202 does not affect the operation of medical imaging system 100. Thus, the medical imaging system 100 can operate in a degraded mode while actor 202 is reset (e.g., actor 202 restarting itself). As a result, the corresponding severity level value for actor 202 in idle state is stored in the pre-defined configuration file. For example, for an error that allows a degraded mode of operation, the severity level may be, for example, a "4" on a scale of 1 to 4, with "1" being the least severe and "4" being the most severe. In another case, in any state for actor 204, if the severity of the fault is high, a system level restart is required for all the states defined. As a result, the corresponding severity level value for actor 204 in all defined states is stored in a pre-defined configuration as "1."

In various embodiments of the invention, four possible severity levels may be provided and defined (e.g., defining the corresponding action and operation of the system corresponding to the severity level). It should be noted that the various embodiments are not limited to four severity levels, but may include more or less, as desired or needed (e.g., based on the medical imaging system). Additionally, the responses or actions to be taken for each severity level may be modified as desired or needed (e.g., based upon the type of application corresponding to an actor). In one exemplary embodiment, severity level 1 may be defined as, but not limited to, a fault or error requiring restarting of medical imaging system 100. This state may occur if, for example, it is determined that as a result in a fault in an actor, the hardware as well as the operating system of medical imaging system 100 require a reboot. The different levels and corresponding actions to be taken may be determined, for example, based on operating conditions, the type of system, system level testing, historical data, etc. Severity level 2 may be defined as, but not limited to, a fault or error requiring an application level reset. The actor having a fault corresponding to a severity level of "2" is restarted and all its related, dependent and/or interdependent actors are reinitialized or restarted. Severity level 3 may be defined as, but not limited to, a fault or error requiring only an actor level reset. The actor having the severity level "3" fault is restarted, while the related, dependent and/or interdependent actors are notified of the fault and their operations may be halted. The severity level 4 may be defined as, but not limited to, a fault or error allowing a degraded mode operation. The actor having the severity level "4" fault is restarted, while the related, dependent and/or interdependent actors, as well as the other components of medical imaging system 100 operate in a degraded mode. The degraded mode may include, for example, a mode of operation wherein the CPU time is provided partially to physical subsystem 102 and physical subsystem 104 for performing operations. The remaining CPU time is utilized for returning medical imaging system 100 to a stable state of operation.

FIG. 5 shows an exemplary configuration file that assigns severity values to, for example, actor 202 and actor 204 in accordance with an exemplary embodiment of the invention and that may be implemented by medical imaging system 100. The file defines a fault recovery function "FAULT_RE-COVERY." Specifically, the function receives input values such as, the ping time-interval, the name of the actors (e.g., actor 202 and actor 204), the stable states of medical imaging system 100 (e.g., idle, application setup, exam-started). Further, based on the response of actor 202 and actor 204 in various states, fault severity values may be defined. For example, a fault value "{IDLE, Actor202, SEV_3}" relates to severity level 3 response of fault in actor 202 in the idle state. The configuration file includes mapping for each type of fault that may be present in medical imaging system 100. As described above, the configuration file captures the state in which a fault may potentially occur for an actor and the type of recovery to be performed based on the fault.

Figure 6:
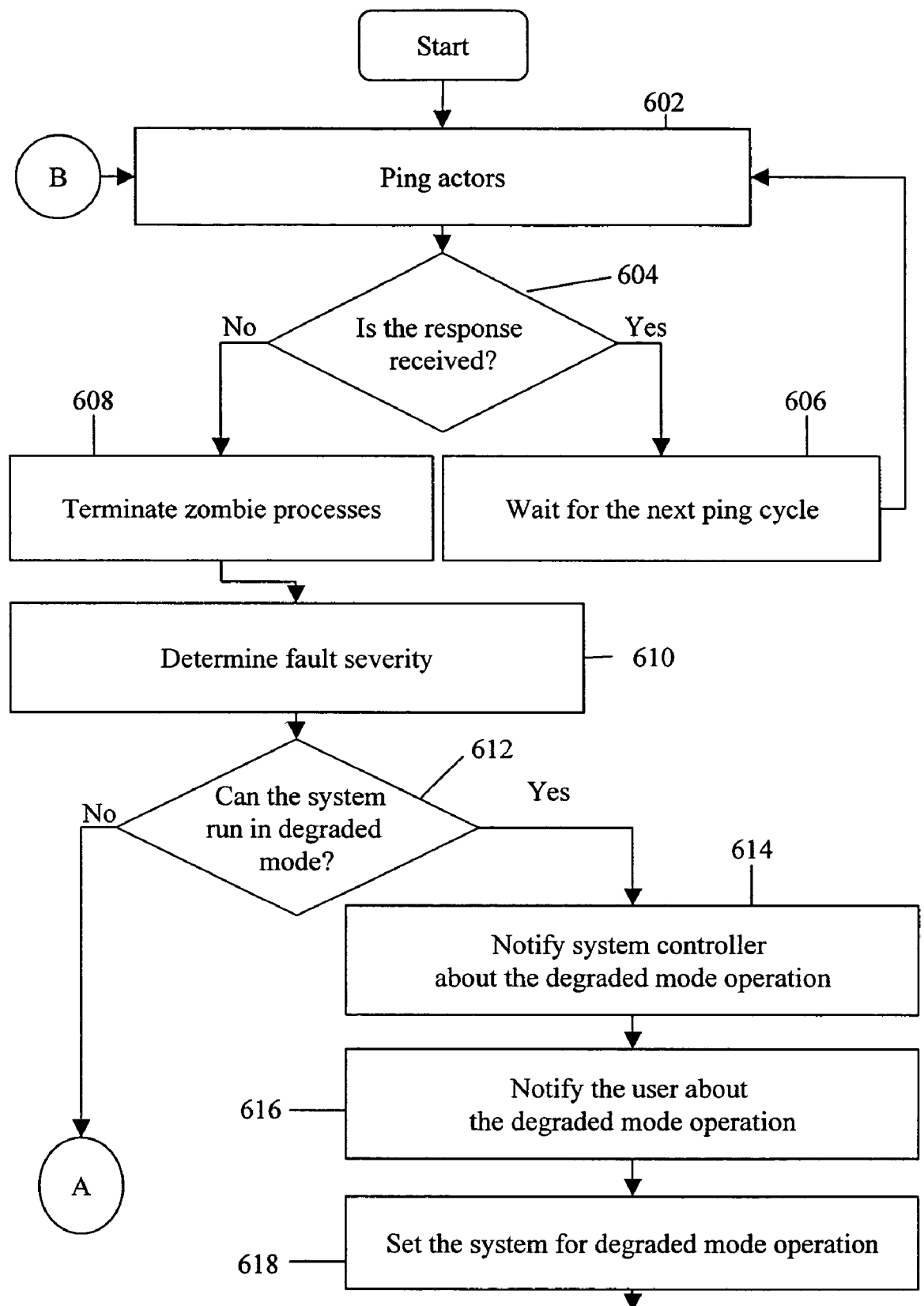
FIGS. 6A and 6B show a flowchart of a process for fault handling and recovery of a medical imaging system in accordance with an exemplary embodiment of the invention.
Figure 6:
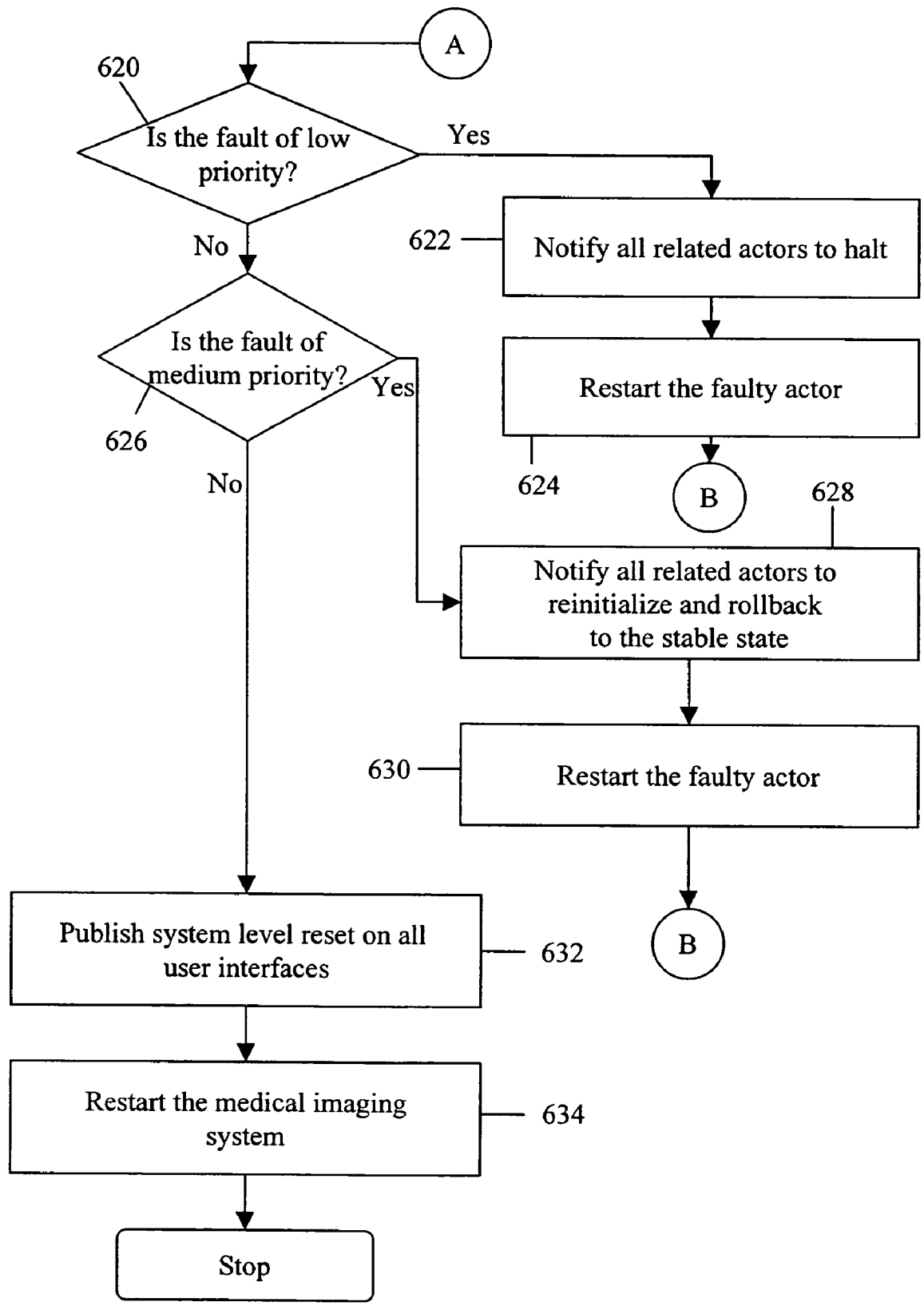

FIG. 6 is a flowchart of a process 600 for fault handling and recovery of a medical imaging system 100 in accordance with an exemplary embodiment of the invention. The flowchart is described in connection with physical subsystem 102 and its subcomponents. However, it should be noted the process of the flowchart may be implemented in connection with other components of medical imaging system, such as, for example, physical subsystem 104 and other subsystems of various embodiments of medical imaging system 100. Specifically, at 602, subsystem controller 108 pings the registered actors (e.g., as registered in location registration component 304), for example, actor 202 and actor 204. In various embodiments, the ping request is sent after a predefined time interval, which may vary based on the requirements of medical imaging system 100. At 604, subsystem controller 108 then waits for a response from actor 202 and actor 204. If a response is received, at 606, subsystem controller 108 waits for the next ping request. This process is repeated until a response is not received form actor 202 and actor 204. For example, subsystem controller 108 iteratively goes back to 602 and pings these actors.

At 604, if no response is received from actor 202 and/or actor 204, the at 608, all zombie or hung processes for the non-responding actor are terminated by subsystem controller 108. This step is performed to halt any operations or functions being performed by the non-responding actor.

After terminating the actors not responding, subsystem controller 108, at step 610, retrieves information regarding the state of medical imaging system 100, and the corresponding severity level of the fault in that state, for example, from a table stored in a memory of medical imaging system 100. The information regarding the severity level of the fault in a particular state may be retrieved, for example, from the configuration file. Based on the severity level of the fault, at 612, subsystem controller 108 determines if the actor having the fault has severity level 4 in that particular state of medical imaging system 100. If the severity level is 4, at 614, subsystem controllers 108 notifies system manager 106 that a degraded mode of operation is required. At 616, in response to this notification, system manager 106 notifies users on user interface 212 and user interface 214 regarding the fault. At 618, system manager 106 then sets medical imaging system 100 in a degraded mode of operation. At 619, only the actor having the fault is restarted or reinitialized, while the other actors in medical imaging system 100 perform their operations. In the degraded mode, for example, the other actors and their operations may be allocated lesser CPU time. The remaining CPU time is used to restore medical imaging system 100 to a stable state.

At 612, if subsystem controller 108 determines that the fault is not of severity level 4, at 620, it determines if the fault is a severity level 3 fault. If the fault is of a severity level 3, then at 622 subsystem controller 108 notifies system manager 106 of the fault, and in response system manager 106 notifies all the related actors of the actor(s) having this fault to halt operation. In addition, at 624, the actor having the fault is restarted or reinitialized. Thus, at 622, the functioning of related actors is halted so that no error is developed in their functioning due to an error in the actor having the fault. After the actor having a fault is restarted or reinitialized, the halted actors return to normal operation in a stable state. In addition, system controller 108 returns to 602 and performs the process 600 again iteratively.

At 620, if subsystem controller 108 determines that the fault is not of severity level 3, at 626, it determines if the fault is a severity level 2 fault. If the fault is of a severity level 3, at 628 subsystem controller 108 notifies system manager 106 of the fault, and in response system manager 106 notifies all the related actors of the actors having a fault to restart or reinitialize. In addition, at 628, the actor having the fault is restarted. While reinitializing, the related actors store their current state and receive input values from the actor having the fault. After the related actor have restarted or reinitialized themselves, medial imaging system 100 returns to a stable state and subsystem controller 108 return to 602 and performs the process 600 again iteratively.

At 626, if subsystem controller 108 determines that the fault is not of severity level 2, at 632, subsystem controller 108 notifies system manager 106 of a system level restart. At 634, system manager 106 notifies the users on user interface 212 and user interface 214 regarding rebooting medical imaging system 100. In a system level reset, the operating system of physical subsystem 102 and physical subsystem 104 are rebooted and medical imaging system 100 starts its operations again.

Various embodiments of the invention provide higher system availability. Recovering the system from faults that at times may not require rebooting the system provides the higher system availability. Thus, a higher number of imaging procedures may be performed per day.

Further, various embodiments of the invention provide higher software reliability. In various embodiments of the invention, the fault management and recovery architecture tracks the fault from its source and restores the component having the fault. Further, various embodiments of the invention provide a configurable medical imaging system. The response of the medical imaging system to a fault can be varied based on the severity of the fault that may occur.

A technical effect of various embodiments of the invention is to categorize the faults based on severity and control the operation of the hardware of the medical imaging system based on the severity of the fault. This reduces system rebooting and provides more system uptime. Another technical effect of various embodiments of the invention to perform recovery of software components over a distributed environment. In a distributed environment, actors of a logical subsystem may be distributed over different physical subsystems. The various embodiments of the invention perform recovery of these related actors over different physical subsystems.

The computer system for implementing the various embodiments as part of a medical imaging system may include a computer, an input device, a display unit and an interface, for example, for accessing the Internet. The computer may include a microprocessor. The microprocessor may be connected to a communication bus. The computer may also include a memory. The memory may include Random Access Memory (RAM) and Read Only Memory (ROM). The computer system further may include a storage device, which may be a hard disk drive or a removable storage drive such as a floppy disk drive, optical disk drive, and the like. The storage device also may be other similar means for loading computer programs or other instructions into the computer system.

The computer system executes a set of instructions that are stored in one or more storage elements, in order to process input data. The storage elements may also hold data or other information as desired or needed. The storage element may be in the form of an information source or a physical memory element within the processing machine.

The set of instructions may include various commands that instruct the processing machine to perform specific operations such as the processes of the various embodiments of the invention. The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

While the invention has been described in terms of various specific embodiments, those skilled in the art will recognize that the invention can be practiced with modification within the spirit and scope of the claims.

What is claimed is:

1. A method for controlling a medical imaging system, said method comprising:
   requesting at predetermined time intervals a response from at least one component within a plurality of subsystems of the medical imaging system;

determining that an error has occurred in the at least one component based upon a failure of the at least one component to respond to the request, wherein said requesting occurs prior to said determining;

identifying at least one subsystem of the plurality of subsystems that includes the at least one component having the determined error;

classifying the determined error as having a severity level selected from a plurality of predetermined severity levels, wherein a response is associated with each severity level of the plurality of predetermined severity levels such that the response for a first severity level of the plurality of predetermined severity levels is different than the response for a second severity level of the plurality of predetermined severity levels;

storing information relating to the determined error, wherein the information includes information usable for the at least one component having the determined error to be restored to a stable state; and restoring automatically, using the response associated with the severity level of the classified determined error, the at least one component having the determined error to the stable state, wherein the stable state includes at least one of a system idle, an application setup, and an exam-started state, and wherein said requesting and said determining are performed by a subsystem controller.

2. A method in accordance with claim 1 further comprising notifying a user of the determined error.

3. A method in accordance with claim 1 wherein said restoring automatically comprises restoring automatically the at least one component having the determined error based on stored data relating to the stable state.

4. A method in accordance with claim 1 wherein said requesting is performed at a time period associated with a type of the at least one component.

5. A method in accordance with claim 1 wherein said restoring automatically comprises at least one of restarting, resetting, rebooting and reinitializing the at least one component having the determined error.

6. A method in accordance with claim 1 further comprising disabling at least one operation of the at least one component having the determined error.

7. A method in accordance with claim 1 wherein the plurality of predetermined severity levels includes a degraded mode operation level, a low severity level, a medium severity level and a high severity level.

8. A method in accordance with claim 7 wherein said restoring automatically comprises resetting automatically, while the identified subsystem in which the at least one component having the determined error is located is operating, only the at least one component having the determined error in the identified subsystem if the determined error is classified with the degraded mode operation level.

9. A method in accordance with claim 7 wherein said restoring automatically comprises resetting automatically only the at least one component having the determined error in the identified subsystem if the determined error is classified with the low severity level.

10. A method in accordance with claim 7 wherein said restoring automatically comprises resetting the at least one component having the determined error in the identified subsystem if the determined error is classified with the medium severity level.

11. A method in accordance with claim 7 wherein said restoring automatically comprises performing automatically a system level restart if the determined error is classified with the high severity level.

12. A method in accordance with claim 11 further comprising notifying a user that the determined error has been classified with the high severity level to facilitate the user controlling the system level restart.

13. A method in accordance with claim 1 further comprising storing recovery data for at least one stable state of a plurality of stable states for restoring the at least one component in the subsystem having the determined error.

14. A method in accordance with claim 1 further comprising registering the at least one component as being associated with a corresponding subsystem of the plurality of subsystems to facilitate identifying the corresponding subsystem in which the determined error is located.

15. A method in accordance with claim 1 further comprising configuring the restoring based on the severity level of the determined error.

16. A method in accordance with claim 1 wherein the at least one component includes at least one of a software component and a hardware component.

17. A method in accordance with claim 1 further comprising associating an actor with each of the at least one component.

18. A method for controlling a medical imaging system, said method comprising:

identifying a plurality of components of subsystems of the medical imaging system;

requesting at predetermined time intervals a response from each component of the plurality of components;

determining that one or more components of the plurality of components failing to respond within a predetermined time period indicates an error associated with the one or more components failing to respond, wherein said requesting occurs prior to said determining;

classifying the determined error as having a severity level selected from a plurality of predetermined severity levels, wherein a response is associated with each severity level of the plurality of predetermined severity levels such that the response for a first severity level of the plurality of predetermined severity levels is different than the response for a second severity level of the plurality of predetermined severity levels;

storing information relating to the determined error, wherein the information includes information usable for the one or more components failing to respond to be restored to a stable state;

performing a reset of the one or more components failing to respond; and restoring to the stable state the one or more components failing to respond based on the severity level of the error, wherein the stable state includes at least one of a system idle, an application setup, and an exam-started state, and wherein said requesting and said determining are performed by a subsystem controller.

19. A method in accordance with claim 18 wherein said performing a reset comprises performing one of a component reset, an application level reset and a system level reset based on the severity level of the determined error.

20. A method in accordance with claim 18 wherein said restoring to the stable state comprises accessing stored information relating to the stable state.

21. A method in accordance with claim 18 further comprising halting operations associated with the one or more components failing to respond.

22. A medical imaging system comprising:

a plurality of subsystems each having at least one component;

a subsystem controller for each subsystem of said plurality of subsystems, said subsystem controller communicating with said at least one component, said subsystem controller configured to:

request at predetermined time intervals a response from said at least one component;

determine, after the request occurs, that an error has occurred in said at least one component based upon a failure of said at least one component to respond to the request;

classify the determined error as having a severity level selected from a plurality of predetermined severity levels, wherein a response is associated with each severity level of the plurality of predetermined severity levels such that the response for a first severity level of the plurality of predetermined severity levels is different than the response for a second severity level of the plurality of predetermined severity levels;

perform a reset of said at least one component; and restore automatically said at least one component having the determined error; and a system manager communicating with each said subsystem controller of said plurality of subsystems and configured to communicate the failure to respond to each said subsystem controller.

23. A medical imaging system in accordance with claim 22 wherein said at least one component comprises software and hardware components and an actor associated with each of said software and hardware components.

24. A medical imaging system in accordance with claim 22 wherein said subsystem controller is configured to perform the reset based on the severity level.

25. A medical imaging system in accordance with claim 24 wherein the reset comprises one of a component reset, an application level reset and a system level reset.

26. A medical imaging system in accordance with claim 22 wherein said plurality of subsystems comprises at least one of a physical subsystem and logical subsystem.

27. A medical imaging system in accordance with claim 22 further comprising a location registration component for identifying a subsystem of said plurality of subsystems in which said at least one component having the determined error is located.

28. A medical imaging system in accordance with claim 22 wherein said subsystem controller further comprises a subsystem manager.

29. A medical imaging system in accordance with claim 28 further comprising at least one user interface, said system manager configured to communicate the determined error to said at least one user interface based upon the failure to respond.

30. A medical imaging system in accordance with claim 22 wherein said subsystem controller is further configured to reset a first component of said at least one component in a first subsystem of said plurality of subsystems based upon the failure to respond of a second component of said at least one component in a second subsystem of said plurality of subsystems.

* * * * *